US 6,590,072 B2

(12) United States Patent
Diers

(10) Patent No.: US 6,590,072 B2
(45) Date of Patent: Jul. 8, 2003

(54) METHOD FOR EXTRACTIVE REFOLDING OF SCRAMBLED SINGLE-CHAIN POLYPEPTIDES

(75) Inventor: Ivan Diers, Vaerlose (DK)

(73) Assignee: NNA/S, Bagsvaerd (DK)

(*) Notice: Subject to any disclaimer, the term of this patent is extended or adjusted under 35 U.S.C. 154(b) by 0 days.

(21) Appl. No.: 09/767,986

(22) Filed: Jan. 23, 2001

(65) Prior Publication Data

US 2002/0086973 A1 Jul. 4, 2002

Related U.S. Application Data

(63) Continuation of application No. PCT/DK00/00713, filed on Dec. 20, 2000.
(60) Provisional application No. 60/174,658, filed on Jan. 6, 2000.

(30) Foreign Application Priority Data

Dec. 22, 1999 (DK) .......................... 1999 01845

(51) Int. Cl.[7] .................. A61K 38/28; C07K 14/00; C12P 21/00
(52) U.S. Cl. .................. 530/303; 530/324; 530/350; 435/69.1; 435/70.1
(58) Field of Search .................. 435/69.1, 69.4, 435/69.7, 70.1, 71.1, 303, 324; 530/399, 412, 427, 344, 402, 350

(56) References Cited

U.S. PATENT DOCUMENTS

| 4,916,212 A | 4/1990 | Markussen et al. ........ 435/69.4 |
| 5,952,461 A | 9/1999 | Kim et al. .................. 530/305 |
| 5,986,048 A | * 11/1999 | Rubroder et al. ............ 530/303 |
| 6,033,875 A | 3/2000 | Bussineau et al. .......... 435/69.4 |

FOREIGN PATENT DOCUMENTS

| CA | 2008245 | 7/1990 |
| CA | 2110442 | 6/1994 |
| CA | 2245151 | 2/1999 |
| JP | 4-144695 | 5/1992 |
| JP | 04-144695 | 5/1992 |
| WO | WO 96/32407 | 10/1996 |

OTHER PUBLICATIONS

Steiner & Clark., Proc Natl, Acad. Sci, vol. 60, pp. 622–629 (1968).
Frank, et al., Rich & Gross., pp. 729–738 (1981).
Russell A. Brierley., Methods Mol Biol., vol. 103., pp 149–177 (1998).
S.O. Kim, et al., Methods Mol Biol., vol. 11., pp. 85–89 (1997).
Jan Markussen., Excerpta Medica, Amsterdam–Oxford., pp. 50–61 (1979).
Jan Markussen., Int J Peptide Protein Res., vol. 25., pp. 431–434 (1985).
Chang, et al., Biochem J., vol. 329., pp 631–635 (1998).
Hua, et al., J Mol Biol., vol. 277, pp. 103–118 (1998).

* cited by examiner

*Primary Examiner*—Gary Kunz
*Assistant Examiner*—Ruixiang Li
(74) *Attorney, Agent, or Firm*—Richard W. Bork, Esq.; Reza Green, Esq; Marc A. Began, Esq.

(57) ABSTRACT

The present invention relates to a method for extractive refolding of scrambled and/or polymerised single-chain polypeptides or proteins into their native conformation directly from a microbial fermentation broth.

26 Claims, No Drawings

METHOD FOR EXTRACTIVE REFOLDING OF SCRAMBLED SINGLE-CHAIN POLYPEPTIDES

This application is a continuation of application serial no. PCT/DK 00/00713 filed on Dec. 20, 2000 and claims priority under 35 U.S.C. 119 of Danish application PA 1999 01845 filed Dec. 22, 1999, and U.S. provisionial application No. 60/174,658 filed on Jan. 6, 2000, of the contents of which are fully incorporated herein by reference.

FIELD OF INVENTION

The present invention relates to a method for extractive refolding of scrambled and polymerised single-chain polypeptides and proteins into their native conformation directly from a microbial fermentation broth.

BACKGROUND OF THE INVENTION

Many polypeptides or proteins feature one or more intra molecular disulfide bonds serving to lock the tertiary conformation in place. If such polypeptides or proteins are recovered with incorrectly positioned disulfide bonds, they are often less biologically active than the corresponding molecule with correct disulfide bonds. Such scrambled or polymerised products are often found in proteins and polypeptides formed by fermentation of recombinant microorganisms or during the growth of a mammalian cell culture and may accumulate, stabilised by the incorrect disulfide bonds. The incorrect disulfide bonds may be intramolecular, giving rise to a misfolded monomeric product, or intermolecular, giving rise to dimeric or polymeric products.

The desired product and its accompanying, incorrectly formed, by-products may be secreted from the cells and found in soluble form in the broth. The may also be found in the periplasm as incorrectly folded and aggregated products resembling insoluble inclusion bodies. This will typically be the case when yeast is being used as the host organism for the recombinant production.

Alternatively, the desired product and its accompanying, incorrectly formed, by-products may be found either in the periplasm or inside the cells, in the form of insoluble inclusion bodies. This is the case when many polypeptides or proteins such as human proinsulin are expressed in $E.$ $coli$ Formation of such scrambled or polymerised by-products may be caused by a number of factors, e.g. that the conditions in the production host, such as pH, temperature, redox potential, concentration and type of chaperones etc. are different from those in the original (natural) site of production. Alternatively, the rate of production may be to high to cope with the time necessary for the molecule to fold into the native conformation which is usually believed to be the state having the lowest free energy. These scrambled and polymerised by-products represent a serious loss in commercial production. Therefore great efforts have been exerted to extract and refold these incorrectly folded proteins.

Thus, Steiner and Clark, Proc. Nat. Acad. Sci. 60, 622–629, 1968, disclose a method for isolation of reduced proinsulin and oxidation of the reduced form to native proinsulin; EP 600372 discloses a method for dissolving and extracting reduced proinsulin from $E.$ $coli$ inclusion bodies after cell homogenisation; EP 906918 discloses an improvement of this process by dilution of the reduced and extracted product in water; Frank, Pettee, Zimmerman and Burck, in: Peptides, Synthesis—Structure—Function, Proceedings of the Seventh American Peptide Symposium, Eds.: Rich, Gross, Pierce Chemical Company, Rockford, Ill., pp 729–738, 1981, describe a process in which human proinsulin is recovered from $E.$ $coli$ via its purified hexa S-sulfonate; WO 96/32407 discloses an unfolding and refolding process of secreted IGF-1; Markussen, in: Proinsulin, Insulin, C-Peptide, Proceedings of the Symposium on Proinsulin, Insulin and C-Peptide, Eds.: Baba, Kaneko, Yanaihara, Excerpta Medica, Amsterdam-Oxford, pp 50–61, 1979, discloses reduction of a single-chain des (B30) insulin precursor; Markusen, in: Int. J. Peptide Protein Res. 25, 431–434, 1985 compares refolding of a mini-proinsulin B(1–29)-A(1–21) and porcine insulin by air oxidation of the reduced and isolated forms of the molecules; and U.S. Pat. No. 6,003,875 discloses a method for improving the yield of IGF-1 when secreted from a yeast cell. A common feature with the prior art is that rather harsh conditions are used in the unfolding/refolding steps and that chaotropic agents are used requiring additional purification steps.

SUMMARY OF THE INVENTION

The present invention relates to a simple method for extractive refolding of scrambled and/or polymerised single-chain polypeptides or proteins to their native conformation directly from a microbial fermentation broth, in which they may appear in a variety of scrambled, misfolded and polymer forms together with the native, monomolecular form.

In the process according to the present invention, the sulphur chemistry is conducted directly on the crude product in the broth from the fermentation or, in the case the scrambled products are retained inside the cells, after disruption of the cell walls.

Thus, the present inventions is related to a method for extractive refolding scrambled and/or polymerised single-chain polypeptides contained in a microbial culture broth said method comprising the following steps:

a) adjusting pH of the culture broth to approximately 10–11;

b) adding a catalyst for refolding of disulfide bonds without adding a chaotropic agent;

c) adjusting pH if necessary;

d) centrifugation of the culture broth to separate cells and cell debris;

e) subjecting the supernatant to oxidation;

f) and isolating single-chain polypeptide material with correctly positioned disulfide bonds by suitable purification steps.

Steps a) to f) may be conducted in a temperature interval from about 4 to about 35° C. or from about 20 to about 25° C. and may be completed within a period from about 30 to about 180 minutes or from about 30 to 120 minutes. The order of one or more of steps a) to e) may be changed or reversed and some of the steps may even be omitted, e.g. step c). Thus in one embodiment, cells and cell debris are removed prior to step b). The catalyst for refolding disulfide bonds is typically a thiol compound, such as cysteine, HCl.

In one embodiment the present invention is related to a process comprising the following steps:

a) adjusting pH of the culture broth to approximately 10–11 by addition of diluted alkali hydroxide;

b) adding a thiol to the culture broth;

c) adjusting pH if necessary;

d) centrifugation of the culture broth to separate cells and cell debris;

e) stirring the supernatant under aeration;

f) and isolating single-chain polypeptide material with correctly positioned disulfide bonds by suitable purification steps.

In still another embodiment the present invention is related to a process comprising the following steps:

a) adjusting pH of the culture broth to approximately 10–11 by addition of 0.1–8 M sodium hydroxid;

b) adding solid or liquid cysteine, HCl to the culture broth to make 0.5–100 mM;

c) after a short period, e.g. 5 minutes, adjusting pH to about 7.0–11.0 if necessary;

d) centrifugation of the culture broth to separate cells and cell debris;

e) stirring the supernatant under aeration for a period of about 30 to about 180 minutes; and f) and isolating single-chain polypeptide material with correctly positioned disulfide bonds by suitable purification steps.

In step a) the culture broth is advantageously diluted with water either before, simultaneously or after adjustment of pH. In one embodiment of the present invention, dilution of the culture broth is accomplished by addition of diluted alkali hydroxide. The dilution of the culture broth in step a) may be from about 2 to about 500%, from about 2 to about 300%, from about 2 to about 200%; from about 5 to 200%; from about 50 to 200% or from about 50 to 150%. Very high yields are obtained at a dilution of about 50%.

Thus in a further embodiment, the present invention is related to a method for extractive refolding scrambled and/or polymerised single-chain polypeptides or proteins contained in a microbial culture broth said method comprising the following steps:

a) adjusting pH of the culture broth to approximately 10–11;

a1) dilution of the culture broth to from about 2% to 500%;

b) adding a catalyst for refolding of disulfide bonds without adding a chaotropic agent;

c) adjusting pH if necessary;

d) centrifugation of the culture broth to separate cells and cell debris;

e) subjecting the supernatant to oxidation;

f) and isolating single-chain polypeptide material with correctly positioned disulfide bonds by suitable purification steps.

The refolded single-chain polypeptides or proteins from step e) will be subjected to suitable purification steps. Thus step f) may cover direct chromatography of the solution from step e) or precipitation by isoelectric precipitation, salting-out or by crystallisation.

The refolded polypeptide may be the desired end product or it may be an intermediate or precursor for the desired end product. The present invention includes a final step wherein the intermediates or precursors are converted into the desired end product by suitable means.

The process according to the present invention is particularly well suited for single chain human insulin precursors or human insulin analogue precursors which are expressed and secreted from yeast cells as described in further detail below. After completion of the unfolding/refolding process the single chain insulin precursors or single chain insulin analogue precursors are converted into insulin or an insulin analogue by suitable means such as in vitro conversion as disclosed in further details below.

Thus, in another embodiment, the present inventions is related to a method for extractive refolding scrambled and/or polymerised single-chain insulin precursors or insulin precursor analogues contained in a microbial culture broth said method comprising the following steps:

a) adjusting pH of the culture broth to approximately 10–11;

b) adding a catalyst for refolding of disulfide bonds without adding a chaotropic agent;

c) adjusting pH if necessary;

d) centrifugation of the culture broth to separate cells and cell debris;

e) subjecting the supernatant to oxidation;

f) isolating the single-chain insulin precursor or insulin precursor analogue with correctly positioned disulfide bonds by suitable purification steps;

g) and converting the insulin precursor or insulin precursor analogue into human insulin or a human insulin analogue by suitable enzymatic conversion steps.

DETAILED DESCRIPTION OF THE INVENTION

Abbreviations and Nomenclature

As used herein the term "thiol compounds" comprises compounds such as cysteine, mercaptoethanol, glutathione, dithiothreitol, or salts or mixtures thereof.

As used herein the term "single-chain polypeptides and proteins" is meant to comprise a single peptide strand constituted of codable amino acid residues. The single-chain polypeptides will contain at least 2 cysteine residues. Examples of single-chain polypeptides are human proinsulin and human proinsulin analogue precursors. Polypeptides and proteins produces by fermentation of transformed microorganisms containing inserted DNA coding for the desired polypeptide or protein or a precursor therefore are the primary targets.

As used herein the term "scrambled" is meant to comprise polypeptides containing disulfide bonds other than those found in the native polypeptide or protein when formed during the natural biosyntheses, inside or outside the native cells.

By "microbial culture broth" is meant the culture broth obtained after cultivation of the microorganism comprising DNA encoding the desired product and still containing cells and cell debris.

With "extractive refolding" is meant a process where expressed polypeptides or proteins associated or bond to the cell wall and/or entrapped in the periplasmic space are released to the culture broth.

With the term "chaotropic agents" is meant a compound that is capable of breaking hydrogen bonds in an aqueous solution such as urea, and guanidinium hydrochloride.

By "connecting peptide" or "C-peptide" is meant the connection moiety "C" of the B-C-A polypeptide sequence of a single chain preproinsulin-like molecule. Specifically, in the natural insulin chain, the C-peptide connects position 30 of the B chain and position 1 of the A chain. A "mini C-peptide" or "connecting peptide" such as those described herein, connect B29 or B30 to A1, and differ in sequence and length from that of the natural C-peptide.

With "desB30", "B'" or "B(1–29)" is meant a natural insulin B chain lacking the B30 amino acid residue, "A(1–21)" or "A" means the natural insulin A chain, "B(1–29)-A(1–21), B28 Asp" means a single-chain insulin precursor with aspartic acid at position 28 of the B-chain and no C-peptide (B29 is linked to A1). This insulin analogue is also called "insulin aspart". With "B'A" is meant a single chain insulin precursor with B(1–29) linked directly to the A chain of insulin.

By "insulin precursor" is meant a single-chain polypeptide which by one or more subsequent chemical and/or enzymatic processes can be converted into human insulin.

By "insulin precursor analogue" is meant an insulin precursor molecule having one or more mutations, substitutions, deletions and or additions of the A and/or B amino acid chains relative to the human insulin molecule. The insulin analogues are preferably such wherein one or more of the naturally occurring amino acid residues, preferably one, two, or three of them, have been substituted by another codable amino acid residue. In one embodiment, the instant invention comprises analogue molecules having position 28 of the B chain altered relative to the natural human insulin molecule. In this embodiment, position 28 is modified from the natural Pro residue to one of Asp, Glu, Lys, or Ile. In a preferred embodiment, the natural Pro residue at position B28 is modified to an Asp residue. In another embodiment Lys at position B29 is modified to Pro; Also, Asn at position A21 may be modified to Ala, Gln, Glu, Gly, His, Ile, Leu, Met, Ser, Thr, Trp, Tyr, Trp or Val, in particular to Gly, Ala, Ser, or Thr and preferably to Gly. Furthermore, Asn at position B3 may be modified to Lys. Further examples of insulin precursor analogues are des(B30) human insulin, insulin analogues wherein $Phe^{B1}$ has been deleted; insulin analogues wherein the A-chain and/or the B-chain have an N-terminal extension and insulin analogues wherein the A-chain and/or the B-chain have a C-terminal extension. Thus one or two Arg may be added to position B 1. Also, position 8 in the B chain may be modified to Asp or Trp and the position 11 in the B chain may be modified to Val.

The single-chain insulin precursors and insulin precursor analogues may be expressed with an N-terminal amino acid residue extension, as described in U.S. Pat. No. 5,395,922, and European Patent No. 765,395A. The N-terminal extension may be removed from the recovered refolded single-chain insulin precursor or insulin precursor analogue by means of a proteolytic enzyme which is specific for a basic amino acid (e.g. Lys) so that the terminal extension is cleaved off at the Lys residue. Examples of such proteolytic enzymes are trypsin or *Achromobacter lyticus* protease I.

After the single chain insulin precursor or insulin precursor analogue has been subjected to the defolding/refolding steps a)–f) it will be subjected to various in vitro procedures to remove the possible N-terminal extension sequence and to remove a possible connecting peptide or C-peptide to give insulin or the desired insulin analogue. Such methods include enzymatic conversion by means of trypsin or an *Achromobacter lyticus* protease in the presence of an L-threonine ester followed by conversion of the threonine ester of the insulin or insulin analogue into insulin or the insulin analogue by basic or acid hydrolysis as described in U.S. patent specification Ser. No. 4,343,898 or 4,916,212.

The single-chain insulin precursor or insulin precursor analogue may feature a peptide bridge linking residue Lys B29 to Gly A1, or they may feature a bridge or connecting peptide having from 1 to 36 amino acid residues. The insulin precursor or insulin precursor analogue may typically have a connecting peptide of from 1 to 5 or from 1 to 3 amino acids residues.

In another embodiment the single-chain protein or polypeptide may be IGF-I, hGH, or factor VII.

The pH value in step a) may be adjusted to about 10.5. Furthermore, the thiol added in step b) may be β-mercaptoethanol, glutathione, dithiothreitol, or salts or mixtures hereof. The thiol may be added in an amount to make from 0.2 to 100 mM; from 1 to 100 mM; from 2 to 100 mM; from 2 to 50 mM; from 2 to 25 mM; from 2 to 15 mM; or from 2 to 5 mM in the culture broth. The thiol is typically added directly to the culture broth but may also be added after cells and cell debris have been removed e.g. by centrifugation. In another embodiment, the thiol is added after disruption of the cells, e.g. when the expressed single-chain polypeptide is not secreted from the cells.

In yet another embodiment the present invention relates to a method in which the temperature of step a) is adjusted from about 10 to 30° C., and in a still further embodiment the temperature of step a) is from about 15 to about 25° C.

In a further embodiment the present invention relates to a method in which step a) is completed in a time period from about 1 to about 20 minutes or from about 2 to about 15 minutes. In a further embodiment step a) is completed within about 10 minutes.

It may be necessary to adjust the pH after addition of the thiol in step b). Thus pH may be adjusted to about 8.5–10.2. In another embodiment pH may be adjusted to about 9.7.

The oxidation in step e) may be accomplished by adding air or oxygen to the supernatant from the previous step. Sufficient oxidation may also be accomplished without any special measurements. In the latter case oxidation is accomplished by aerating of the supernatant during stirring.

The method according to the present invention may be carried out in a scale from about 10 $m^3$ to about 1000 $m^3$. The method may be a continuous method with average holding times as described above for the batch operations.

The present invention is described in further detain in the following examples which are not in any way intended to limit the scope of the invention as claimed.

EXAMPLES

General Procedures

Measurements pRedox: The redox potential was measured on a Radiometer PHM61 meter by a calomel/Pt electrode and calibrated daily against a commercial standard buffer #209881250 using the standardisation 220 mV at 25° C., pH 7 as for the Ag/AgCl electrode giving a deviation of 11 mV. The difference between our measurement values (E) and the standard redox potential $E_H$ is $E_H$=E+211 mV.

pH: Measured with a Radiometer PHM 83 Autocal pH-meter daily calibrated with pH 4,00 and 7,01 buffers (Radiometer) and frequently checked with a corresponding pH 11,00 buffer.

HPLC: The method of analysis is based on the separation of the insulin aspart precursor from non-related product present in the fermentation broth and during the purification steps, by use of reversed-phase high-performance liquid chromatography (RP-HPLC). In RP-HPLC the separation is obtained based on differences in hydrophobicity of the individual components.

The content of precursor is calculated from the area registered at 214 nm compared with the area of a human insulin reference with known content. As the absorption at 214 nm is a measure of the peptide bonds, the quantification is based on content by weight (mg per liter, mg/l).

Equipment: HPLC equipment for gradient elution consisting of the following units: One or two pumps for eluent mixing; degassing facilities for the eluents, e.g. helium; an auto sampler; column heater facilities, a detector for registration at 214 nm, and data handling facilities (integration of peak areas). A HPLC column: YMC C18, 120 A, 5μm, 125×4.0 mm I.D. (Novo Nordisk) or other appropriate C18 column may be used.

Reagents: Eluent A: 0.2 M $Na_2SO_4$(2.8% w/w) 0.04 M $H_3PO_4$(0.4% w/w) 10.0 % v/v (7.7% w/w) acetonitrile, pH 2.3:

Preparation of 5000 ml eluent can be conducted as follows: Weigh out 142.0 g of $Na_2SO_4$ and dissolve it in approximately 4000 ml of Millipore Milli-Q purified water in a 5000 ml volumetric flask. Add 13.5 ml of $H_3PO_4$ and adjust pH to 2.30 with ethanolamine. Add 390.0 g of acetonitrile and fill up with Millipore Milli-Q purified water to 5000 ml and mix carefully. The eluent is filtered (0.45 μm) and degassed.

Eluent B: 42.8% (w/w) acetonitrile in water: Preparation of 4000 g eluent can be conducted as follows: Weigh out 1712.0 g of acetonitrile and add Millipore Milli-Q purified water to 4000 g and mix it. The eluent is degassed before use.

Sample Preparation

As described in example 1

| RP-HPLC conditions | |
| --- | --- |
| Flow: | 1 ml/min. |
| Temperature: | 40° C. |
| Detection: | 214 nm |
| Elution: | Gradient |
| Initial conditions: | % B is adjusted aiming at a retention time (Rt) for human insulin of approximately 20 min. |
| Gradient: | Linear increase of 13% B during 20 min. |

Example

| | |
| --- | --- |
| Initial: | 37% B |
| 0–20 min: | Linear increase to 50% B |
| 20–20.1 min: | Linear decrease to 37% B |
| 20.1–25 min: | Equilibration at 37% B |
| The run time is 25 min. | |

$OD_{600}$:
Measured on a single beam Pye-Unicam SP6-550 spectrophotometer after dilution to an OD between 0,1 and 0,5. Measure for macroscopic impurities and colour.

$OD_{290}$:
Measured on a single beam Pye-Unicam SP6-550 spectrophotometer after dilution to an OD between 0,1 and 0,5. Measure for low molecular impurities in the near UV-range as proteins and nucleic acids.

Example 1

The *Saccharomyces cerevisiae* strain MT663 was used as host to produce single chain mini-proinsulins (or ICP or IGF-I) as previously decribed by Markussen et al, U.S. Pat. No. 4,916,212 and Kjeldsen et al. (Gene 170, 107–112, 1996). The DNA encoding the mini-proinsulins was synthesized by overlap extension polymerase reactions (PCR) using appropriate designed oligomers and cloned into the expression cassette of the vector described by Kjeldsen et al. The plasmid DNA was transformed into MT663, and transformants selected on YPD plates. The MT663 transformant designed to produce B(1–29)-A(1–21), B28Asp was designated YJB155. A culture broth was prepared by continuous culture of YJB155 in a 2 liter fermentor on a medium consisting of essential salts and vitamins and yeast extract and glucose as carbon source and ammonia as nitrogen source at pH 5,5, 30° C., D=0,08 h-1. The overflowing broth was collected in a 10 liter vessel kept over ice and stored in the fridge (4° C.) before extraction. Before extraction the sample was homogenised by fast stirring (500 rpm) on a magnetic stirrer, Ika-combimag Reo using a 25 mm long triangular (14 mm side) teflon impeller. 100 ml of broth was sampled and the temperature was slowly adjusted to room temperature, 22° C. 3 ml of 4 M NaOH diluted with water to a final volume of 50 ml was quickly mixed with the broth at a high stirring rate (700 rpm) to reach pH 10.5. Then 0.3 g of cysteine, HCl was added and after 1–2 minutes the cysteine was brought in solution and pH adjusted from 10.8 to 10.5 by addition of 0.44 ml 4 M HCl. The stirrer speed was now reduced to 300 rpm and kept constant for another 10 minutes. Now pH was lowered to 9.7 by addition of 0.53 ml 4 N HCl and the culture centrifuged at 4000 rpm for 5 minutes. The supernatant was removed and stirred as before and no further pH adjustment was necessary (pH 9.7). The air oxidation was completed 51 minutes after the beginning of the refolding experiment. Samples were taken at 0 (after dilution) (sample 2); before acidification to pH 9.7 at 11.5 minutes (sample 3); after centrifugation (at 21 minutes) (sample 4); and at the end (at 51 minutes) (sample 5) and all immediately acidified to pH 3 with HCl and run on HPLC to quantify the yield of insulin precursor.

The results are given in Table 1, compared to a direct determination on the culture broth at pH 5.5 (sample 1).

TABLE 1

| Sample # | 1 | 2 | 3 | 4 | 5 |
| --- | --- | --- | --- | --- | --- |
| Time, min | | 0 | 11.5 | 21 | 51 |
| pH | 5.5 | 10.8 | 10.5 | 9.7 | 9.7 |
| Yield mg/liter | 36.9 | 53.1 | 38.1 | 61.9 | 81.4 |
| OD290 | 24.8 | | | | 41.1 |
| OD600 | 2.6 | | | | 7.4 |

Example 2

Effect of Dilution.

In 5 experiments using the same culture broth as in Example 1, the initial dilution was varied from 2.5% using 8 M NaOH to 50%, 100%, 150% and 200% by addition of the corresponding amount of water to the diluted NaOH. To have a constant concentration of 5 mM cysteine in the reaction mixture, varying amounts of cysteine, HCl were added. Except for the temperature, which was kept at 25° C. in a water bath, all other conditions were as described in example 1. The results are shown in Table 2.

TABLE 2

| | (Yields in mg/l) | | | | |
| --- | --- | --- | --- | --- | --- |
| Dilution % | 1 (direct) | 2 | 3 | 4 | 5 |
| 2.15 | 36.3 | 52.7 | 52.3 | 85.3 | 86.8 |
| 50 | 36.3 | 44.6 | 32.9 | 93.4 | 111.2 |
| 100 | 36.3 | 47.6 | 38.8 | 98.8 | 113.6 |
| 150 | 36.3 | 52 | 43.5 | 83.5 | 122.4 |
| 200 | 36.3 | 50.4 | 46.8 | 92 | 127.1 |

Example 3

Effect of dilution at constant cysteine amount: The 300 ml culture broth was diluted 25% with 75 ml of NaOH in water to pH~10.5 and immediately made 5 mM in cysteine by addition of 0.4 g of cysteine, HCl. The culture was now divided in three parts of which two parts were diluted further to 50 and 100% with pure water. Temperature was not kept constant and rose from 19° C. to 22° C. through the experiment. The results are shown in Table 3.

TABLE 3

(Yields in mg/l)

| Dilution % | 1(direct) | 2 | 3 | 4 | 5 |
|---|---|---|---|---|---|
| 25 | 32.3 | 76.8 | 43.6 | 92.3 | 93.1 |
| 50 | 32.3 | 50.4 | 69.2 | 108.9 | 115.2 |
| 100 | 32.3 | 69.6 | 99.2 | 134.9 | 137.5 |

Example 4

Effect of Temperature.

Experiments made in water bath and the temperature was kept at 15° C., 20° C. and 25 ° C. in a thermostat. All other conditions were as in example 1. The results are shown in Table 4.

TABLE 4

(Yields in mg/l)

| Temp ° C. | 1(direct) | 2 | 3 | 4 | 5 |
|---|---|---|---|---|---|
| 15 | 36.3 | 61.2 | 35.5 | 93.3 | 104.9 |
| 20 | 36.3 | 44.6 | 43.1 | 94.8 | 118 |
| 25 | 36.3 | 45.4 | 20.8 | 116.9 | 155.5 |

Example 5

Effect of pH:

a. The test conditions were as follows: pH was adjusted to 10.0±0.1 after primary dilution and addition of cysteine, HCl. The temperature was held at room temperature (measured) and the dilution was 50%. Cysteine, HCl (to 5 mM) was added as powder. Samples were taken as indicated in Table 5 and cells were removed immediately by centrifugation. The supernatants were used for determination of yield by HPLC and impurities released from the cells by measurement of soluble protein, RNA/DNA impurities at OD290 and aggregates/particles at OD600. The results are shown in Table 5.

TABLE 5

| Time, min. | Direct on broth | 0 (after dilution) | 1.5 after addition of cysteine, HCl | 30 | 60 | 120 |
|---|---|---|---|---|---|---|
| pH |  | 9.75 | 9.3 | 10 | 10.1 | 10.1 |
| pRedox |  | — | −375 | −460 | −395 | −455 |
| Stirrer, rpm |  | 700 | 700 to 300 | 300 | 300 | 300 |
| Temp: ° C. |  | 21 | — | 23 | 24.5 | 26 |
| Yield mg/l | 42.1 | 40.8 | 44.1 | 62.6 | 85.1 | 123.2 |
| OD290 | 10.2 | 7 | 11.1 | 15.8 | 20.8 | 39.2 |
| OD600 | 0.57 | 0.65 | 0.22 | 2.17 | 5.36 | 8.8 |

The yield increased remarkably during the run, but so did impurities although many were removed by the last centrifugation of the supernatants adjusted to pH 3. All the figures in Table 5 were from these double centrifuge samples. PAGE-Western analysis on extracted broth showed that the cells were effectively stripped for insulin very fast after the basic reductive conditioning and that an early centrifugation could be just as efficient as the late one shown in this experiment and therefore reduce the amount of impurities which eases the later recovery steps.

b. Carried out as in experiment a. with the following modifications: Temperature 22,5° C., pH adjusted from 10.5 to 9.5 after 15 minutes and all cells removed by centrifugation. Moderate and weak stirrer speed applied during the final oxidation. The results are shown in Table 6.

TABLE 6

| Time, min. | Direct broth | 0 (after dilution) | 1.5 after addition of cysteine | 15 | 30 | 60 | 120 | 30 | 60 | 120 |
|---|---|---|---|---|---|---|---|---|---|---|
| pH |  | 10.7 | 10 | 10.5/9.5 | 9.6 | 9.6 | 9.5 | 9.4 | 9.3 | 9.5 |
| pRedox |  | — | −400 | −460 | −465 | −433 | −407 | — | −370 | −100 |
| Stirrer, rpm |  | 700 | 700 to 300 | 300 | 250 | 250 | 250 | 50 | 50 | 50 |
| Yield mg/l | 50.7 | 55.7 | 57.5 | 41.8 | 131.1 | 140.7 | 148.9 | 123.1 | 123.6 | 127 |
| OD290 | 11.3 | 12.7 | 7.2 | 21.6 | 21.3 | 29.9 | 33.5 | 23.1 | 22.3 | 23.4 |
| OD600 | 0.5 | 0.23 | 0.33 | 1.43 | 1.6 | 4.2 | 3.2 | 3.6 | 3 | 3.1 | c. This experiment was carried out to elucidate the role of the pH during oxidation. The temperature was slightly lower than in the previous experiment, 21° C. The reduced and diluted mixture was treated as described above, but after 16 minutes divided in 3 parts which were each adjusted to its own pH (8.9; 9.3; 9.7). Weak stirring were applied after centrifugation. The results are shown in Table 7.

TABLE 7

| Time, min. | Direct broth | 0 | 5 | 16 | 33 | 48 | 34 | 50 | 35 | 51 |
|---|---|---|---|---|---|---|---|---|---|---|
| pH |  | 11.5 | 10.5 | 10.5/new | 9.7 | 9.7 | 9.3 | 9.3 | 8.9 | 8.9 |
| Yield mg/l | 31.7 | 53.1 | 34.6 | 27.9 | 115.6 | 124 | 105.7 | 110.4 | 95.6 | 91.8 |
| OD290 | 23.6 | 40.1 | 27.8 | 27.5 | 25.3 | 31.8 | 28.8 | 31 | 30.2 | 30.7 |
| OD600 | 4.9 | 9 | 3 | 3.7 | 5.5 | 4.5 | 4.4 | 4.2 | 5.1 | 5.7 |

Cells can be extracted and insulin precursor unscrambled and unfolded and refolded and oxidized without occurrence of further impurities. PH 9.7 seems to be better than 9.3 and 8.9.

Example 6
Effect of Stirring and Aeration:

The culture broth was oxidized under aeration with vigorous, very mild stirring or no stirring. Redox conditions were carefully followed and it was obvious that the oxidation process is taking place as early as in the centrifuge (with no stirring) and that the redox potential stays stable at −400 mV in this stage (data from the previous experiments). If air is bobbled through the mixture, the redox potential rises immediately and no further oxidation of the insulin precursor takes place. Likewise, very vigorous stirring causes the redox potential to increase and finish the oxidation of the product. Mild oxidizing conditions applied by stirring are preferred as exemplified in example 5b.

Example 7
Effect of Scaling up From 100 ml to 3.5 Liters.

The experiments were carried out at 25° C., 5 mM cysteine and 50% dilution to pH 10.5. The first experiment (reference) was conducted as described in example 1 except for the temperature, now held at 25° C. in a water bath with thermostat, and the size of the equipment. The same stirrer was used, and a 42 mm long triangular impeller. The results are shown in Table 8.

TABLE 8

| (100 ml) | | | | | |
|---|---|---|---|---|---|
| pH | 4.9 | 10.7 | 10.5 | 9.6 | 9.6 |
| pRedox |  | −420 | −455 | −310 | −40 |
| Yield | 72.6 | 21.2 | 21.5 | 139.8 | 171.2 |

In the next experiment 3.5 liters broth were used and all additions scaled up with a factor of 35. Because the surface area was relatively lowered the experiment was continued for 3 hours compared to the 50 minutes used above. The results are shown in Table 9.

TABLE 9

| (3.5 liters) | | | | | | | | | |
|---|---|---|---|---|---|---|---|---|---|
| Time, min. | Direct | 0 | 10 | 20 | 50 | 110 | 140 | 170 | 200 |
| pH | 4.9 | 10.5 | 10.5 | 9.7 | 9.6 | 9.6 | 9.6 | 9.6 | 9.7 |
| Yield, mg/l | 72.6 |  |  |  | 131.1 | 135.3 | 144.6 | 144.3 | 158 |

This experiment was repeated with 3.0 liter of fresh culture broth. This time a redox electrode was installed and because the potential never dropped the experiment was run over night. Results are shown in Table 10.

TABLE 10

| (3 liters) | | | | | | | | | |
|---|---|---|---|---|---|---|---|---|---|
| Time, min. | Direct | 0 | 10 | 20 | 50 | 110 | 140 | 170 | 1100 | 1280 |
| PH | 4.8 | 10.4 | 10.5 | 9.4 | 9.4 | 9.4 | 9.4 | 9.4 | 9.3 | 9.2 |
| PRedox |  | −400 | −450 | −420 | −430 | −430 | −430 | −422 | −48 | −36 |
| Yield, mg/l | 44.3 | 41.6 | 38.8 | 90.2 | 97.3 | 101.7 | 105.7 | 99.1 | 107.8 | 105.6 |

Example 8
Other Insulin Analogues:

By use of appropriate oligomers DNA encoding a number of other mini-proinsulin analogues was constructed and expressed in the same *S. cerevisiae* host system as previously described. The following insulin precursor analogues were tested: Glu(GluAla)$_3$GluProLys(SEQ ID NO: 1)-B'A, B8Trp; Glu(GluAla)$_3$GluProLys(SEQ ID NO: 1)-B'A, B8Asp; Glu$_3$ProLys(SEQ ID NO: 2)-B'A,B11Val; and Glu(GluAla)$_3$-ProLys(SEQ ID NO: 3)-B'-AlaAlaLys-A(1–21), B21Trp. Fermentation and extractive refolding were carried out as described in example 7. The results are shown in Table 11.

TABLE 11

| Precursor | Mutation | Yield before refolding mg/l | Yield after refolding mg/l |
|---|---|---|---|
| Glu(GluAla)3GluProLys(SEQ ID NO: 1)-B'A | B8Trp | 4.6 | 25.7 |
| Glu(GluAla)3GluProLys(SEQ ID NO: 1)-B'A | B8(Asp) | 32.2 | 50.5 |
| Glu3ProLys(SEQ ID NO: 2)-B'A | B11Val | 11.1 | 22.1 |
| Glu(GluAla)3ProLys(SEQ ID NO: 3)-B'-AlaAlaLys-A(1-21) | B21Trp | 4.3 | 5.7 |

Example 9
Refolding of ICP

Construction of an ICP (human insulin A- and B-chain connected with the C-peptide from human IGF-I) was described by Kristensen et al, Biochem J 305, 981–986 (1995). A culture broth was prepared and treated as described in example 7. 5833 g of culture broth at pH 4.8, with a content of ICP of 16.3 mg/l, was adjusted to pH 10.5 with an 2916 g of weak NaOH. Then 4.21 g of cysteine, HCl was added and the culture broth was vigorously stirred for a couple of minutes. After 10 minutes pH was adjusted to 9.7 with 1 N HCl and the cells were spun down on a Beckman g cooling centrifuge at 4000 rpm at 10° C. for 15 minutes. The supernatant (7122 g) was then aerated at room temperature for 30 minutes by slow stirring. The yield of ICP was 71.2 mg.

Example 10
Refolding of IGF-I

An S. cerevisiae strain producing Human IGF-I was made as described by Kristensen et al, Biochem J., 305, 981–986 (1995). A culture broth was prepared and treated as described in example 1. The results are shown in Table 12.

TABLE 12

| Sample # | 1 | 2 | 3 | 4 | 5 |
|---|---|---|---|---|---|
| pH | 5.26 | 10.9 | 10.7 | 9.7 | 9.5 |
| pRedox |  | −460 | −475 | −232 | −41 |
| Yield, mg/l | 6.9 | 0 | 13.8 | 16.0 | 22.8 |

All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

What is claimed is:

1. A method for extractive refolding scrambled and/or polymerised single-chain polypeptides contained in a microbial culture broth, the method comprising in the following order the steps of:
   a) adjusting pH of the culture broth to approximately 10–11;
   b) adding a catalyst for refolding of disulfide bonds without adding a chaotropic agent;
   c) adjusting pH if necessary;
   d) centrifugation of the culture broth to separate the cells;
   e) subjecting the supernatant to oxidation;
   f) and isolating single-chain polypeptide material with correctly positioned disulfide bonds by suitable purification steps.

2. The method of claim 1, wherein adjusting the pH in step a) is by addition of diluted alkali hydroxide.

3. The method of claim 1, wherein the culture broth is diluted from about 2% to about 500% in step a).

4. The method of claim 1, wherein the catalyst for refolding of disulfide bonds in step b) is a thiol compound.

5. The method of claim 4, wherein the thiol compound is selected from the group consisting of cysteine, mercaptoethanol, glutathione, and dithiothreitol, and mixtures thereof.

6. The method of claim 5, wherein the thiol compound is added in a concentration of from about 0.2 to about 100 mM.

7. The method of claim 5, wherein the thiol compound is added in a concentration of from about 1 to about 50 mM.

8. The method of claim 5, wherein the thiol compound is added in a concentration of from about 2 to about 5 mM.

9. The method of claim 5, wherein the thiol compound is cysteine, HCl.

10. The method of claim 1, wherein step a) is conducted at a temperature from about 4 to about 35° C.

11. The method of claim 1, wherein step a) is conducted at a temperature from about 10 to about 30° C.

12. The method of claim 1, wherein step a) is conducted at a temperature from about 15 to about 25° C.

13. The method of claim 1, wherein the reaction time for step a) is from about 1 to about 20 minutes.

14. The method of claim 13, wherein the reaction time is from about 5 to about 15 minutes.

15. The method of claim 14, wherein the reaction time is about 10 minutes.

16. The method of claim 1, wherein the pH in step c) is adjusted to about 8.5–10.2.

17. The method of claim 16, wherein pH in step c) is adjusted to about 9.7.

18. The method of claim 1, wherein the supernatant in step e) is subjected to aeration.

19. The method of claim 1, wherein steps a) to e) are completed in from about 30 to about 120 minutes.

20. The method of claim 1, where the single-chain polypeptide is a human insulin precursor or a human insulin precursor analogue.

21. The method of claim 20, wherein the insulin precursor or insulin precursor analogue comprises a peptide bridge of up to 15 amino acid residues in length linking the amino acid residue in position B29 in the B chain to the amino acid residue in position A1 in the A chain.

22. The method of claim 21, wherein the peptide bridge linking the amino acid residue in position B29 in the B chain to the amino acid residue in position A1 in the A chain is of up to 5 amino acid residues in length.

23. The method of claim 22, wherein the peptide bridge linking the amino acid residue in position B29 in the B chain to the amino acid residue in position A1 in the A chain is of up to 3 amino acid residues in length.

24. The method of claim 20, wherein the insulin precursor analogue comprises Asp in position B28.

25. The method of claim 20, wherein the insulin precursor analogue comprises Lys in position B28 and Pro in position B29.

26. The method of claim 20, wherein the insulin precursor analogue comprises Gly in position A21.

* * * * *